United States Patent
Suri (10) Patent No.: US 8,805,043 B1
(45) Date of Patent: Aug. 12, 2014

(54) SYSTEM AND METHOD FOR CREATING AND USING INTELLIGENT DATABASES FOR ASSISTING IN INTIMA-MEDIA THICKNESS (IMT)

(75) Inventor: Jasjit S. Suri, Roseville, CA (US)

(73) Assignees: Jasjit S. Suri, Roseville, CA (US); Atheropoint LLC, Roseville, CA (US)

(*) Notice: Subject to any disclaimer, the term of this patent is extended or adjusted under 35 U.S.C. 154(b) by 641 days.

(21) Appl. No.: 12/799,177

(22) Filed: Apr. 20, 2010

Related U.S. Application Data (63) Continuation-in-part of application No. 12/798,424, filed on Apr. 2, 2010, now abandoned.

(51) Int. Cl.
*G06K 9/00* (2006.01)
*A61B 8/08* (2006.01)

(52) U.S. Cl.
CPC .......................................... *A61B 8/52* (2013.01)
USPC .......................................................... 382/131

(58) Field of Classification Search
CPC .......................................................... A61B 8/52
USPC .......................................................... 382/131
See application file for complete search history.

(56) References Cited

U.S. PATENT DOCUMENTS

| | | | |
|---|---|---|---|
| 5,734,739 A | 3/1998 | Sheehan et al. | |
| 6,132,373 A | 10/2000 | Ito et al. | |
| 6,251,072 B1 | 6/2001 | Ladak et al. | |
| 6,267,728 B1 | 7/2001 | Hayden | |
| 6,597,937 B2 | 7/2003 | Liu et al. | |
| 6,614,453 B1 | 9/2003 | Suri et al. | |
| 6,718,055 B1 | 4/2004 | Suri | |
| 6,785,409 B1 | 8/2004 | Suri | |
| 6,813,373 B1 | 11/2004 | Suri et al. | |
| 6,817,982 B2 | 11/2004 | Fritz et al. | |
| 6,835,177 B2 | 12/2004 | Fritz et al. | |
| 6,842,638 B1 | 1/2005 | Suri et al. | |
| 6,845,260 B2 | 1/2005 | Liu et al. | |
| 6,913,888 B2 * | 7/2005 | Schwartz et al. | 435/6.16 |
| 7,020,314 B1 | 3/2006 | Suri et al. | |
| 7,024,027 B1 | 4/2006 | Suri et al. | |
| 7,272,241 B2 | 9/2007 | Demi et al. | |
| 7,340,083 B2 | 3/2008 | Yuan et al. | |
| 7,353,117 B2 * | 4/2008 | Yuan et al. | 702/19 |
| 7,376,253 B2 | 5/2008 | Spreeuwers et al. | |
| 7,657,299 B2 * | 2/2010 | Huizenga et al. | 600/410 |

(Continued)

FOREIGN PATENT DOCUMENTS

WO     WO03/042921 A     5/2003

OTHER PUBLICATIONS

Koktzoglou, Ioannis. "Development and Assessment of Methods for Vascular Wall and Atherosclerosis Magnetic Resonance Imaging." Northwestern University, 2006. Ann Arbor: ProQuest. Web. May 27, 2014.*

*Primary Examiner* — Sheetal R Rangrej (57) ABSTRACT

A computer-based system for creating and using intelligent databases for assisting in intima-media thickness (IMT) measurements. Various embodiments utilize clinical data (images) to design intelligent clinical data sets, including geometric markers like blood vessel centerline, which can then be used with conventional image processing to compute the intima-media thickness of the carotid walls. The intelligent clinical image data utilizes the demographics (ethnity/race, gender and age) to classify the data. Finally, the intelligent database is used to collect intelligent parameters which are then applied to the incoming patients to estimate their intima-media thickness.

21 Claims, 10 Drawing Sheets

Overall System

(56) References Cited

U.S. PATENT DOCUMENTS

| | | |
|---|---|---|
| 2003/0053669 A1 | 3/2003 | Suri et al. |
| 2005/0043614 A1 | 2/2005 | Huizenga et al. |
| 2005/0119555 A1* | 6/2005 | Fritz et al. ............ 600/410 |
| 2006/0064016 A1 | 3/2006 | Demi et al. |
| 2006/0241465 A1 | 10/2006 | Huennekens et al. |
| 2007/0003116 A1 | 1/2007 | Yuan et al. |
| 2007/0038061 A1 | 2/2007 | Huennekens et al. |
| 2007/0269086 A1 | 11/2007 | Kerwin et al. |
| 2008/0009702 A1 | 1/2008 | Liu et al. |
| 2008/0051658 A1 | 2/2008 | Demi et al. |
| 2008/0095422 A1 | 4/2008 | Suri et al. |

* cited by examiner

Overall System
Figure 1

CAIMT
Figure 2

Alignment System
Figure 3

Wall Sub-System
Figure 4

Centerline Estimation
Figure 5

Off-Line LI / MA Weighted Coefficients

Figure 6

Classification Data Base
Figure 7

Aligned Data Base Design
Figure 8

SYSTEM AND METHOD FOR CREATING AND USING INTELLIGENT DATABASES FOR ASSISTING IN INTIMA-MEDIA THICKNESS (IMT)

CROSS-REFERENCE TO RELATED PATENT APPLICATION

This non-provisional utility patent application is a continuation-in-part patent application of the U.S. patent application Ser. No. 12/798,424, filed Apr. 2, 2010 now abandoned, entitled, "SYSTEM AND METHOD FOR MONITORING ATHEROSCLEROSIS", having common inventors and assigned to the same assignee as the present patent application, the present patent application incorporating by reference the entirety of the referenced parent patent application.

COPYRIGHT

A portion of the disclosure of this patent document contains material that is subject to copyright protection. The copyright owner has no objection to the facsimile reproduction of the patent document or the patent disclosure, as it appears in the Patent and Trademark Office patent files or records, but otherwise reserves all copyright rights whatsoever. The following notice applies to the software and data as described below and in the drawings that form a part of this document: Copyright 2009-2010 Dr. Jasjit S. Suri and Biomedical Technologies Inc., All Rights Reserved.

TECHNICAL FIELD

This application relates to a method and system for use with data processing, data storage, and imaging systems, according to one embodiment, and more specifically, for creating and using intelligent databases for assisting in intima-media thickness (IMT) measurements.

BACKGROUND

Atherosclerosis is a vessel disease which can cause stroke or heart attack. This disease gradually progresses over time if not treated. As a result, this disease progression needs to be monitored. There are several modalities which can be used for understanding the regression and progression of plaque in carotids, coronaries, aorta and other blood vessels. Some the most popular modalities are Magnetic Resonance Imaging (MRI) and Ultrasound.

The state of Atherosclerosis in carotids or other blood vessels can be studied using MRI or Ultrasound. Because ultrasound offers several advantages like real time scanning of carotids, compact in size, low cost, easy to transport (portability), easy availability and visualization of the arteries are possible, Atherosclerosis quantification is taking a new dimension using ultrasound. Because one can achieve compound and harmonic imaging which generates high quality images with ultrasound, it is thus possible to do two-dimensional (2D) and three-dimensional (3D) imaging of carotid ultrasound for monitoring of Atherosclerosis.

In recent years, the possibility of adopting a composite thickness of the tunica intima and media, i.e., an intima-media thickness (hereinafter referred to as an "IMT") of carotid arteries, as an index of judgment of arterial sclerosis has been studied. Conventional methods of imaging a carotid artery using an ultrasound system, and measuring the IMT using an ultrasonic image for the purpose of diagnosis are being developed.

A conventional measuring apparatus can measure an intima-media thickness of a blood vessel using an ultrasound device to scan the blood vessel. Then, for example, an image of a section of the blood vessel including sections of the intima, media and adventitia is obtained. The ultrasound device further produces digital image data representing this image, and outputs the digital image data to a data analyzing device.

The intima, media and adventitia can be discriminated on the basis of changes in density of tissue thereof. A change in density of tissue of the blood vessel appears as a change of luminance values in the digital image data. The data analyzing device detects and calculates the intima-media thickness on the basis of the changes of luminance values in the digital image data. The digital image data can include a plurality of luminance values each corresponding to respective one of a plurality of pixels of the image. The data analyzing device can set a base position between a center of the blood vessel and a position in a vicinity of an inner intimal wall of the blood vessel on the image, on the basis of a moving average of the luminance values. The data analyzing device can detect a maximum value and a minimum value from among the luminance values respectively corresponding to a predetermined number of the pixels arranged from the base position toward a position of an outer adventitial wall on the image. The data analyzing device can then calculate the intima-media thickness on the basis of the maximum value and the minimum value.

Usually, the clinical data gathered from the analysis of IMT in patients are never reused when generated in clinics or hospitals. Examples of this clinical data can include images obtained after ultrasound scanning the diseased or abnormal anatomies, such as blood vessels or other organs. The disease can be Atherosclerosis (or plaque) deposits in the carotid arteries, which causes stroke or heart attack. The risk biomarker for such a disease is the intima-media thickness of the blood vessels in the carotids. The media-adventitia carotid wall is specifically challenging to detect due to the presence of plaque and speckle distribution. But, the clinical data is typically discarded after the diagnosis and/or treatment of a particular patient.

Thus, a system and method for creating and using intelligent databases for assisting in intima-media thickness (IMT) measurements is needed.

BRIEF DESCRIPTION OF THE DRAWINGS

The various embodiments are illustrated by way of example, and not by way of limitation, in the figures of the accompanying drawings in which.

DETAILED DESCRIPTION

In the following description, for purposes of explanation, numerous specific details are set forth in order to provide a thorough understanding of the various embodiments. It will be evident, however, to one of ordinary skill in the art that the various embodiments may be practiced without these specific details.

This patent application discloses a computer-based system and method for creating and using intelligent databases for assisting in intima-media thickness (IMT) measurements. IMT measurement is a very important risk marker of the Atherosclerosis disease. Typically, there are two ways to measure the arterial IMT's: (a) invasive methods and (b) non-invasive methods. In invasive methods, traditionally, intravascular ultrasound (IVUS) is used for measuring vessel wall thickness and plaque deposits where special catheters are inserted in the arteries to image them. Conventional ultrasound is used for measuring IMT non-invasively, such as from brachial and/or femoral arteries. The main advantages of non-invasive methods are: (i) low cost; (ii) convenience and comfort of the patient being examined; (iii) lack of need for any intravenous (IV) insertions or other body invasive methods (usually), and (iv) lack of any X-ray radiation; Ultrasound can be used repeatedly, over years, without compromising the patient's short or long term health status. Though conventional methods are generally suitable, conventional methods have certain problems related to accuracy and reliability.

The IMTs are normally 1 mm in thickness, which nearly corresponds to 15-25 pixels (depending upon the resolution of the image) on the screen or display. IMT estimation having a value close to 1 mm is a very challenging task in ultrasound images. Under normal resolutions, a 1 mm thick media thickness is difficult to estimate using stand-alone image processing techniques. Over and above, the image processing algorithms face an even tighter challenge due to the presence of speckle distribution. The speckle distribution is different in nature from these interfaces. This is because of the structural information change between intima, media and adventitia layers of the vessel wall. As a result, the sound reflection from different cellular structures is different. The variability in tissue structure—all that happens in 1 mm of the vessel wall—brings fuzziness in the intensity distribution of the vessel wall. Under histology, media and adventitia walls are clearly visible and one can observe even their thicknesses. This 1 mm zone is hard to discern in a normal resolution image of 256×256 pixels in a region of interest (ROI) or in a higher resolution image of 512×512 pixels in a region of interest (ROI). One needs a high resolution image to process and identify the intensity gradient change in ultrasound images from lumen to intima and media to adventitia layers. The ultrasound image resolution may not be strong enough like MRI or computerized axial tomography (CAT or CT) images, which can be meaningful for soft tissue structural information display.

There are two ways to process and identify the intensity gradient change in ultrasound images from lumen to intima (LI) and media to adventitia (MA) layers: (a) have a vascular surgeon draw the LI/MA borders and compute the IMT image interactively, OR (b) have a computer determine the LI and MA borders along with IMT's. Case (a) is very subjective and introduces variability in the IMT estimation. IMT screenings are really part of the regular check-up for patients and millions of scans are done each day around the world. The manual handling of such a repetitive work flow of IMT screenings is tedious and error-prone. Case (b) is difficult to implement, because it is difficult to identify the LI and MA borders with heavy speckle distribution and the inability of ultrasound physics to generate a clear image where the semi-automated or automated image processing methods are used for IMT estimation. However, as described herein, a better method is to use a modification of the second case, where one can still assist the image processing algorithms by introducing knowledge about the anatomy and classifying the nature of the disease and patient demographics. This will ease the burden of finding the LI and MA borders along with IMT estimation. Particular systems and processes for measuring the IMT of a patient are described in the co-pending parent patent application referenced herein.

The systems and methods presented in this patent application are based on the integration of the knowledge gathered from the population based on anatomy, demographics, gender, and age. This patent application combines the high level image processing techniques, such as image alignment, multi-resolution scale-space lumen detection, LI and MA borders in the paradigm of knowledge based on anatomy, demographics, gender and age. Thus, the technique is very insensitive to local regional noise. This offers a great advantage compared to local challenges such as: (a) how well the ultrasound probe is gripped with the neck of a patient to scan the carotids; (b) how well the ultrasound gel is being applied; (c) the orientation of the probe; (d) demographics of the patient; (e) skills of the sonographer or vascular surgeon; and (f) threshold chosen for finding the peaks corresponding to the LI and MA points for each signal orthogonal to the lumen. Computer processing power is used for automatically generating IMT measurements with increased IMT measurement accuracy.

In this patent application as described in view of various example embodiments, we introduce at least the following novel concepts:

(A) Intelligence Knowledge Data Base Reconstruction: we mimic the histologist and a physician (e.g., an ultrasound radiologist or vascular surgeon or an expert sonographer) in detecting the LIMA borders and estimating the IMT;

(B) Ethnicity/Race/Age/Gender Classification/Nature of the Disease: we also introduce a new concept where the mimicking information is assisted by the nature of the disease in a human; and (C) Guiding Marker in Design of the Intelligent Database: we, take advantage of the regional space in the image, which has always shown to have information in it and use that as a guiding marker to estimate the walls of the vessels and IMT.

(A) Intelligence Reconstruction:

In the first concept, the expert sonographer or vascular surgeon actually takes the region of interest in the far wall of the common carotid artery, zooms it and then traces the LI and MA borders. Then, we use a ruler or caliper or any distance measurement device to measure the IMT. In a way, the expert is creating the information about the physical location of the LI and MA borders. This information is not being used again when he tries to estimate the LI/MA borders. This information is not used by other sonographers or other vascular surgeons during the LIMA and IMT estimations. It is only in their mind and not transferred to a non-trained user. The information contained in this trace is valuable and must not be destroyed. In this patent application, we create a database of like or similar information which is created by the vascular surgeon or a trained sonographer or an expert radiologist. This database then builds an intelligence or knowledge base that is based on the learning of the gradient change when looking at the vascular walls. The intelligence gathered is also taking into account so-called inter- and intra-variability. Because this intelligence is gathered by multiple sonographers or vascular surgeons or ultrasound radiologists, this information can be averaged out to create a more meaningful intelligence. Thus, the mimicking information by a histologist or vascular surgeon or an ultrasound radiologist is used for creating an intelligent computer program, which will be used for automatically creating the LI/MA border estimation and IMT measurements.

(B) Ethnicity, Race and Demographics:

In the second concept, this patent application takes advantage of the nature of the disease, which is demographic dependent. Relationships between ethnicity and arterial disease have been shown in prior art studies, where it was shown, for example, that South Asians have stronger Atherosclerosis effect in their arteries. Besides the demographics, socially deprived regions of geography are also a factor which is linked with the demographics and with effects on Atherosclerosis disease in arteries.

Conventional techniques have shown that a maximum internal carotid artery plaque thickness (MICPT) in an average entire sample is 1.5±1.4 mm, increased directly with age, and was greater in whites and blacks than Hispanics. There was a significant interaction between race-ethnicity and low-density lipoprotein (LDL) cholesterol, with a greater effect of increasing LDL cholesterol among Hispanics. Conventional statistics showed that overall MICPT for whites and blacks were 1.7±1.3 mm compared to Hispanics which was 1.2±1.5 mm. MICPT was almost 40% higher in Blacks and Whites compared to Hispanics. This data represents very important studies and concepts for Atherosclerosis and IMT measurement.

Other studies showed excess atherosclerosis in whites with diabetes compared with blacks and Hispanics that was restricted to calcification in the coronary arteries. These results also show that those of Chinese ancestry had smaller IMT compared with other ethnicities. Thus, demographics and ethnicity plays an important role in IMT measurement.

Besides the demographics and geography, another major factor which helps to classify the nature of the disease is the gender of the patient. Studies have shown that atherosclerotic plaques in women, compared with those in men, contained significantly more cellular fibrous tissue, both in native coronary arteries. One study showed a link between LTL (Leukocyte telomere length) and Atherosclerosis as determined by the IMT measurement using ultrasound. This study showed that LTL is relatively shorter in individuals who have high evidence of cardiovascular disease. The study concluded that in obese men, shortened LTL is a powerful marker of increased carotid IMT. This means higher IMT is for obese men. Now that the obesity is being rated as a current epidemic, IMT measurement has become a very important risk biomarker. Another study showed that Retinal arteriolar narrowing is related to risk of coronary heart disease (CHD) in women, but not in men. Such analysis has also been done for men vs. women and compared for carotid IMT evaluations for men vs. women.

(C) Guiding Marker:

In the third concept, this patent application describes a process of taking advantage of the regional space in the image which has always shown to have information in it and use that as a guiding marker to estimate the near or far walls of the vessels and IMT. One conventional technique uses the blood velocity profile for capturing the lumen region. It is also proven that the centerline of such lumen can be estimated given the lumen gradient edge. Centerline methods for estimation of tubes have been very popular in image processing. Conventional computing techniques have been used for computing the centerline of the blood vessel. Other known techniques use a distance transform method for computing the centerline of the blood vessels based on distance transform. Thus, we can see that the centerline of the internal carotid artery can be easily computed. In one example embodiment, the systems and methods described herein use the centerline as a marker both for creating an intelligent database and deriving the average centerline information of the database for patients with the same/similar anatomy, gender, demographics, ethnicity, and age group.

Using these three novel concepts as described above, the various embodiments described herein include a software system which works as described in more detail below. The system is called CAIMT (Completely Automated Intima-Media Thickness). The CAIMT system can take the ultrasound internal carotid B-mode longitudinal scan image data as generated in a clinical setting or office-based settings and compute the LI/MA borders and IMT. The online CAIMT system of an example embodiment is comprised of three components: an alignment system, an initial LI or MA edge estimation system, and a dependency system for LI/MA border estimation. Finally, the CAIMT system includes a ruler or caliper used for IMT estimation. These various sub-systems of the CAIMT system are described in more detail below.

The first component of CAIMT is the alignment system. The alignment system is based on registration of a particular patient's incoming ultrasound B-mode or radio frequency (RF) image scan with one or more average scans of persons with like characteristics (e.g., similar anatomy, demographics, gender, ethnicity, age, etc.). For example, the particular patient will have particular characteristics, such as known anatomy (e.g., internal carotid artery, common carotid artery, femoral artery, brachial artery, or aortic artery), gender (man vs. women), and known ethnicity/race/demographics (e.g., white, black, Chinese, Asian, Indian, 60 years old, etc.). Additionally, an aligned database can be accessed to obtain ultrasound B-mode or RF image scan data corresponding to one or more average scans of average persons with the same gender, ethnicity/race/demographics and other characteristics as the particular patient. The image scan of the particular patient is then aligned with the image scan(s) of average persons with like characteristics. The aligned data is created from the raw database of the ultrasound B-mode or RF scans by aligning all the images of the database with respect to the image whose carotid is the center and nearly horizontal with respect to the x-axis of the image (bottom most edge of the image). After registration, the lumen edges are determined for the aligned incoming ultrasound scan. Because the lumen edges or MA edges of the particular patient can be compared with lumen edges of an average person with like characteristics as obtained from the aligned database, the lumen edge determination can be more accurate and anomalies can be more easily identified.

The MA/LI edges can be computed by using the intelligence IMT data created from the aligned database. This data is in the form of dependency coefficients, which are actually computed by combining the ground truth information from the intelligent database. These MA coefficients are intelligent offline parameters, which are obtained in the first place by combining the observed intelligent LI/MA boundaries and intelligent ground truth MA/LI boundaries or borders of the vessel. Once the CAIMT system estimates the LI and MA borders, one can then estimate the IMT measurements from these two borders. Further details of the CAIMT system are provided below.

Detailed Methodology of the System of an Example Embodiment

Figure 1:
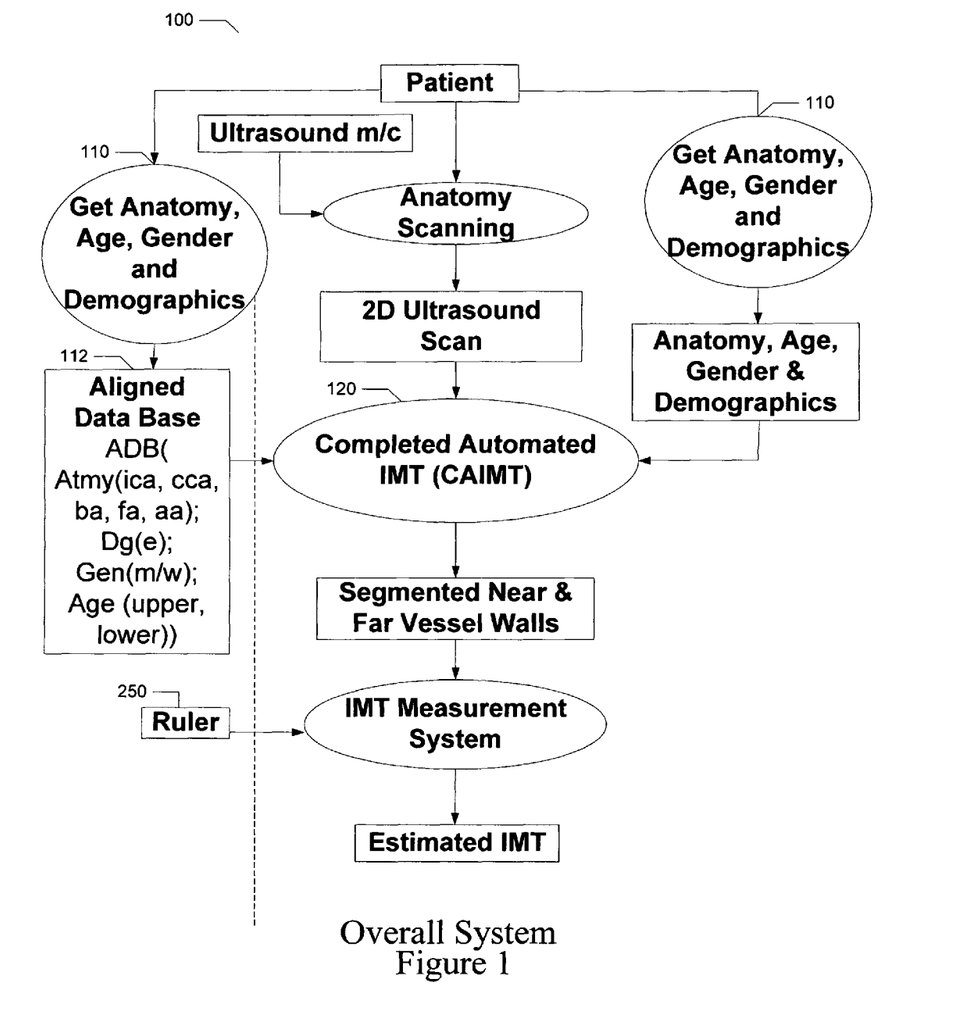
FIG. 1 illustrates an example embodiment of the overall system for creating and using intelligent databases for assisting in intima-media thickness (IMT) measurements.

Overall System:

Referring now to FIG. 1, the overall system 100 of an example embodiment includes collecting the patient information (such as anatomy, ethnicity, race, gender, age, other demographics, etc.) 110 and storing this information in an aligned database system 112. The aligned database system 112 can also include a classification database as described in more detail below. The aligned database system 112 can be used for storage of prior carotid scans for one or more patients and structured based on patient demographics. The database system 112 can also be used for storage of other information, such as the patient demographic information. This complete statistical and visual information for a patient can be used to generate spatial pixel information and related images, which can be made available to a sonographer or vascular surgeon or neuroradiologist or cerebral neuroradiologist or cardiologist, or other system user.

The demographic background of the patient, including anatomy, ethnicity, gender, age, medical history, and the like, can be collected when the patient arrives for the carotid or other anatomical scan. This information can be stored in the database 112 and provided as an input to the CAIMT system 120, which is used for the automated carotid IMT measurement. CAIMT 120 also receives information from the aligned database 112 or intelligent system which sends in the average value of IMT (based on anatomy, ethnicity, demographics, gender, age), and intelligent LI and MA approximations, based on the like characteristics of the patient. CAIMT 120 is an automated system which basically receives and processes patient information. This patient information is also retained in the aligned database system 112. Aligned database system 112 accepts input in the form of patient demographics, such as patient anatomy, age, gender, and ethnicity. Note that the align database system 112 can have multiple databases and finds the closest match for the input. In FIG. 1, aligned database 112 is shown to have four attributes: anatomy, ethnicity (included with demographic information), gender, and age. It will be apparent to those of ordinary skill in the art that other patient attributes or characteristics may similarly be retained in the database 112. Anatomy can be represented by 'Atmy' with parameters, ica, cca, fa, ba, aa, where the symbols represent: internal carotid artery (ica), common carotid artery (cca), femoral artery (fa), brachial artery (ba), and aortic artery (aa). Ethnicity or demographics can be represented as 'dg(e)', where "e" represents the ethnicity, gender is represented as "gen" and age by "age". Gender will have 'man' and 'woman' represented as "m" and "w", hence "gen(m/w)" can be the notation used. Age can have a range defined as "upper" and "lower", thus the age attribute can be represented by "age(upper, lower)". Thus, the aligned database 112 can be represented as: ADB(Atmy(ica, cca, ba, fa, aa); dg(e); gen(m/w); age (upper, lower)). Ethnicity "e" is for White, Black, Chinese (Asian), Indian (Asian), Hispanic, or something similar.

Figure 2:
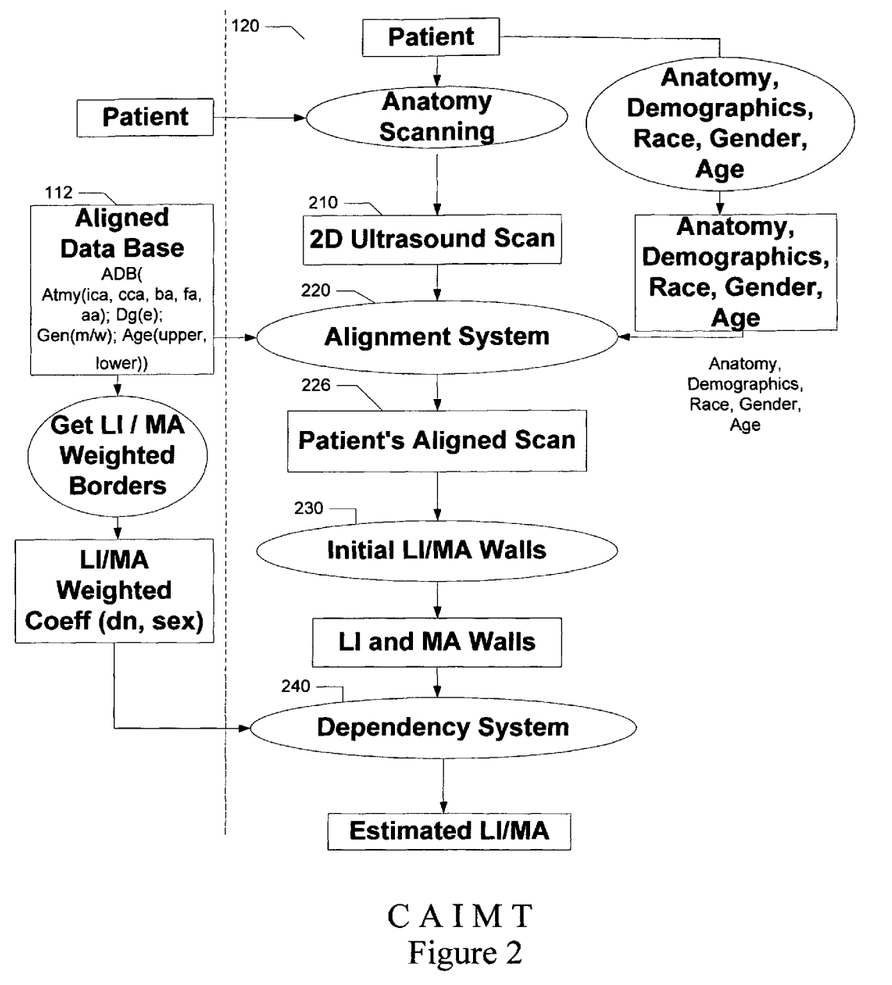
FIG. 2 illustrates an example embodiment of the CAIMT (Completely Automated Intima-Media Thickness) system.

CAIMT (Completely Automated Intima-Media Thickness) System:

Referring now to FIG. 2, the CAIMT system 120 of an example embodiment is shown. The CAIMT system 120 takes the ultrasound internal carotid B-mode or RF longitudinal scan 210 in a clinical setting or office-based settings and computes the LI/MA borders and IMT. The online CAIMT system 120 in an example embodiment comprises three main components: alignment system 220, initial LI or MA edge estimation system 230, and the dependency system for LI or MA border estimation 240. Finally, a ruler 250 can be used for IMT estimation.

Figure 3:
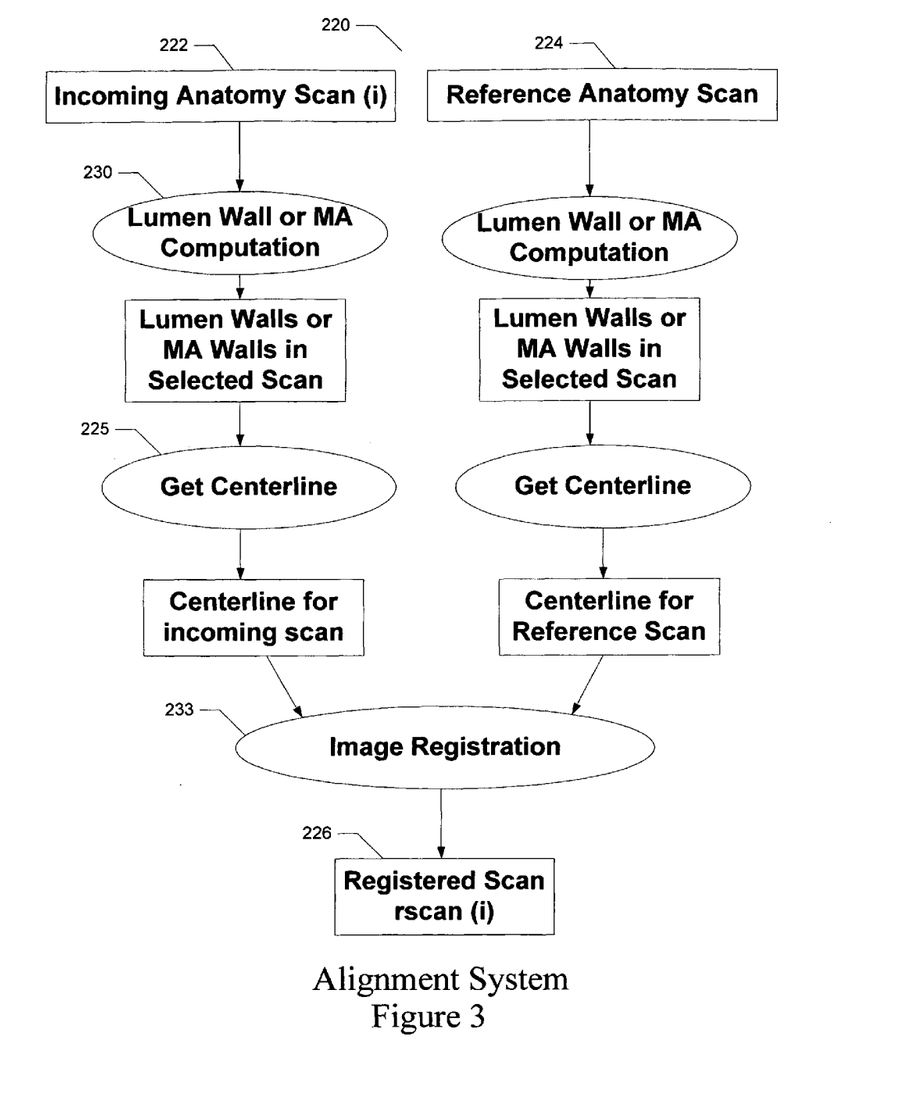
FIG. 3 illustrates an example embodiment of the Alignment sub-system for Images.

Referring now to FIG. 3, one component of CAIMT 120 is the alignment system 220. The input to the CAIMT system 120 includes the ultrasound scan along with Atmy (ica, cca, fa, ba, aa), dg(e), gen(m/w) and age(low,up) from the aligned database system 112. The output of the aligned data base system (ADB) 112 sends in the LI, MA borders, and IMT values when it finds the best match to a patient with like characteristics. In an example embodiment, the image alignment performed by the alignment system 220 is based on registration of a particular patient's incoming ultrasound B-mode or RF image scan with one or more average scans of persons with like characteristics. For example, the particular patient will have particular characteristics, such as known Anatomy (ica, cca, fa, ba, aa), gender (man vs. women), age, and known ethnicity/race/demographics (e.g., white, black, Chinese, Asian, Indian, 60 years old, etc.). Additionally, the aligned database 112 can be accessed to obtain ultrasound B-mode or RF image scan data corresponding to one or more average scans of average persons with the same anatomy, gender, ethnicity/race/demographics and other characteristics as the particular patient. The image scan of the particular patient is then aligned with the one or more image scans of average persons with like characteristics. The aligned data is created from the raw database of the ultrasound B-mode scans by aligning the images of the database 112 with respect to the image whose carotid is the center and nearly horizontal with respect to the x-axis of the image (bottom most edge of the image). After registration, the lumen or MA edges are determined for the aligned incoming ultrasound scan. Because the lumen or MA edges of the particular patient can be compared with lumen or MA edges of an average person with like characteristics as obtained from the aligned database 112, the lumen or MA edge determination can be more accurate and anomalies can be more easily identified.

Figure 4:
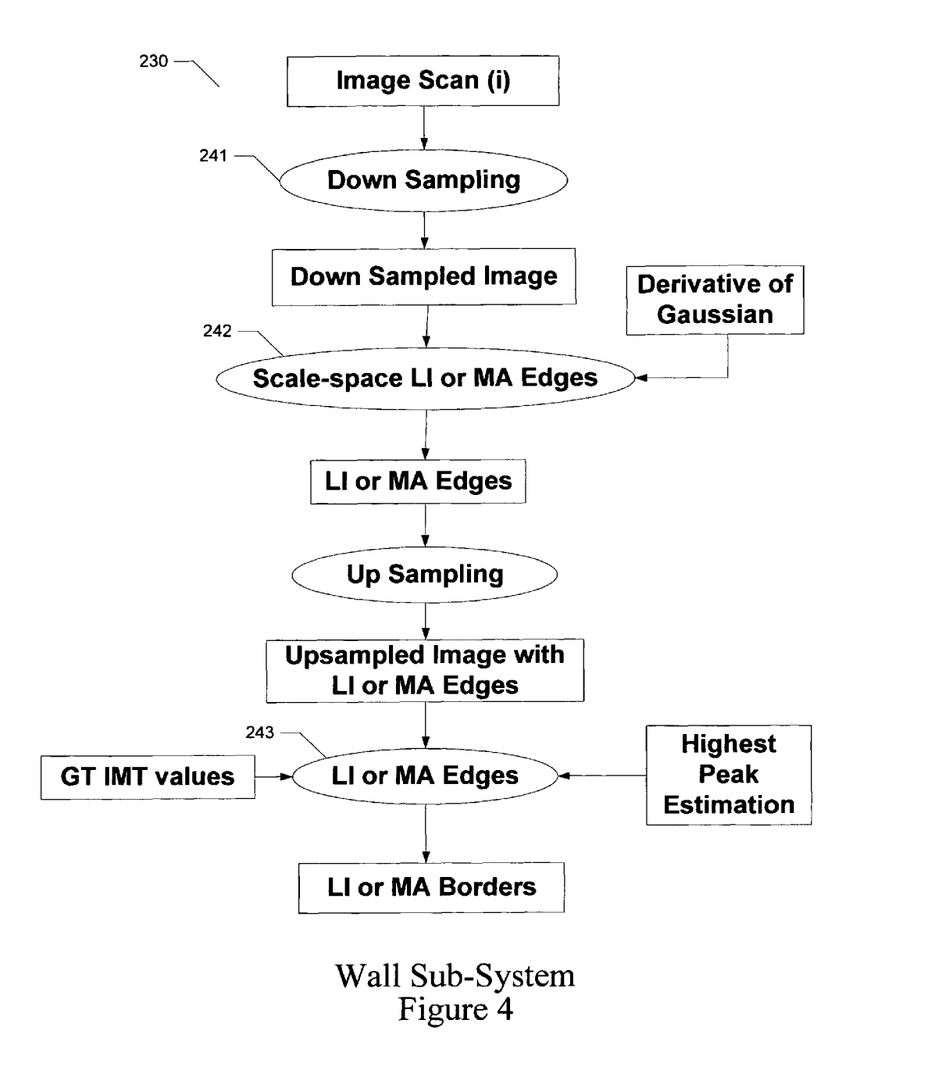
FIG. 4 illustrates an example embodiment of the Wall Subsystem.

Referring now to FIGS. 3 and 4, the LI or MA edges can be computed by using process 230 and the intelligence IMT data created from the aligned database 112. This data is in the form of dependency coefficients, which are actually computed by combining the ground truth information from the intelligent database. These LI or MA coefficients are intelligent offline parameters, which are obtained in the first place by combining the observed intelligent LI boundaries and intelligent ground truth MA boundaries or borders of the vessel. Once the CAIMT system 120 estimates the LI and MA borders, one can then estimate the IMT measurements from these two borders.

One main purpose of the alignment system 220 is to align the online incoming patient scan 222 to the best match reference image 224 in the aligned database 112. Once the best match reference image 224 is found, ADB 112 sends in the LI, MA borders, and the averaged image of the data base 112 for that anatomy, ethnicity, gender, and age group. This is also called the reference image 224, while the floating image 222 comes from the online ultrasound image scan. The alignment system 220 then uses an image registration process 233 to convert the online ultrasound scan 222 to an aligned ultrasound scan 226 for the incoming patient. The alignment protocol of a particular embodiment requires that the alignment system 220 uses process 225 to compute the centerline of the lumen or MA region and uses the centerline as a guiding channel. This means the centerline of the lumen or MA in both floating 222 and reference 224 images are computed by process 225 and the images 222 and 224 are then aligned from both the sources. The new floating image 226 of the incoming patient is then transformed with respect to the reference image 224 from the aligned database 112. In one embodiment, the alignment system 220 gets called by the alignment database 112.

Figure 5:
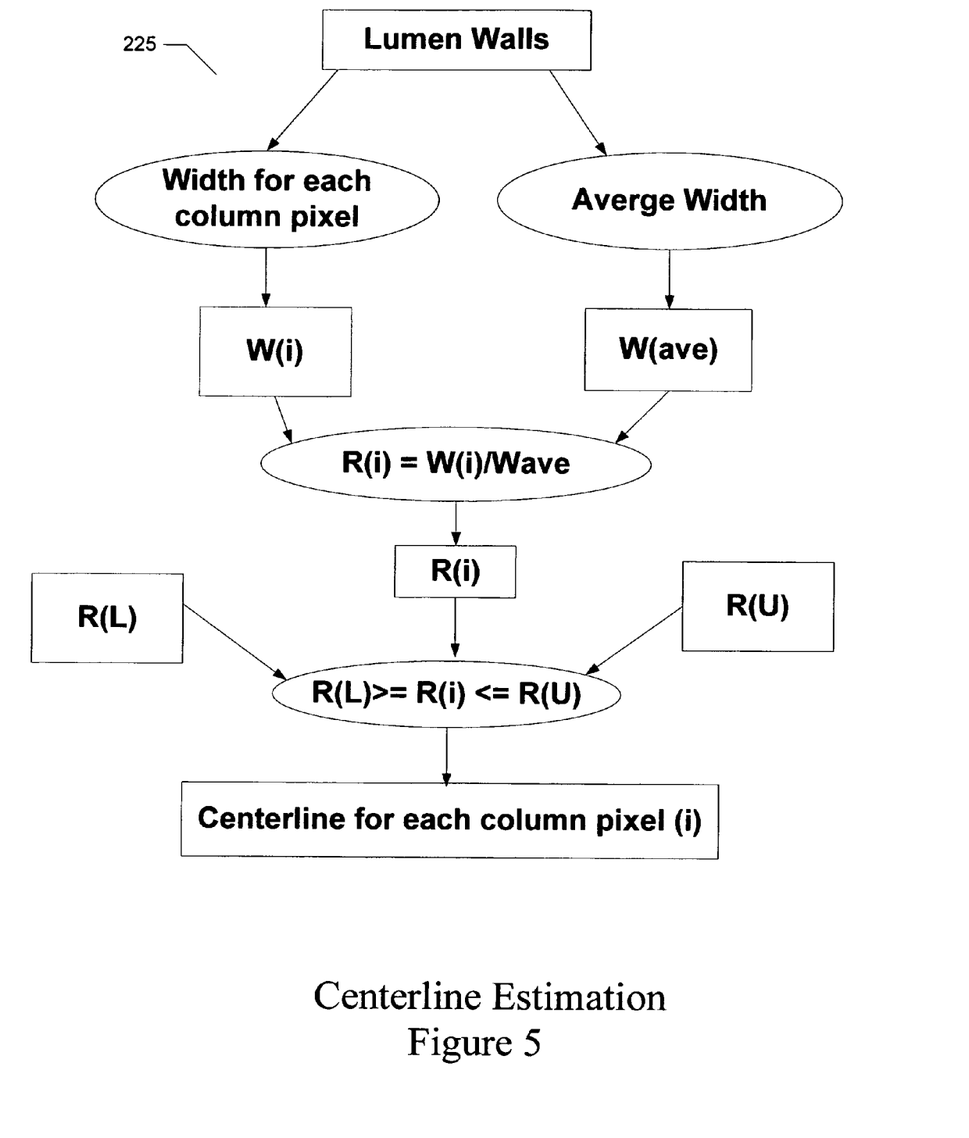
FIG. 5 illustrates an example embodiment of the Centerline Estimation Subsystem.

To summarize the operation of the alignment system 220, the floating image 222 is aligned to the reference image 224. Centerline of the lumen or MA is used as a reference for alignment. As shown in FIG. 5, the centerline can be estimated from the lumen or MA borders by using process 225. These borders can be estimated using a multi-resolution scale-space methodology, such as the example process 230 shown in FIG. 4. In this methodology shown in FIG. 4, the image is down sampled by using process 241 and higher order Gaussian convolutions are run to obtain the lumen edges by using processes 242 and 243 (e.g., see FIG. 4). The center of the lumen or MA edges are the centerlines. The images 222 and 224 are then aligned from both the sources using the centerlines. The new floating image 226 of the incoming patient is then transformed with respect to the reference image 224 from the aligned database 112.

Referring again to FIG. 2, the CAIMT 120 includes an initial LI or MA estimation sub-system 230 that can use a multi-resolution scale-space method. In one embodiment, the aligned image 226 is down sampled and then the lumen or MA edges are computed using the convolutions of the higher order Gaussian derivatives with known sigma. This will immediately give us the edges of the intima-lumen or MA edges. This process, in an example embodiment, is shown in FIG. 4.

Figure 6:
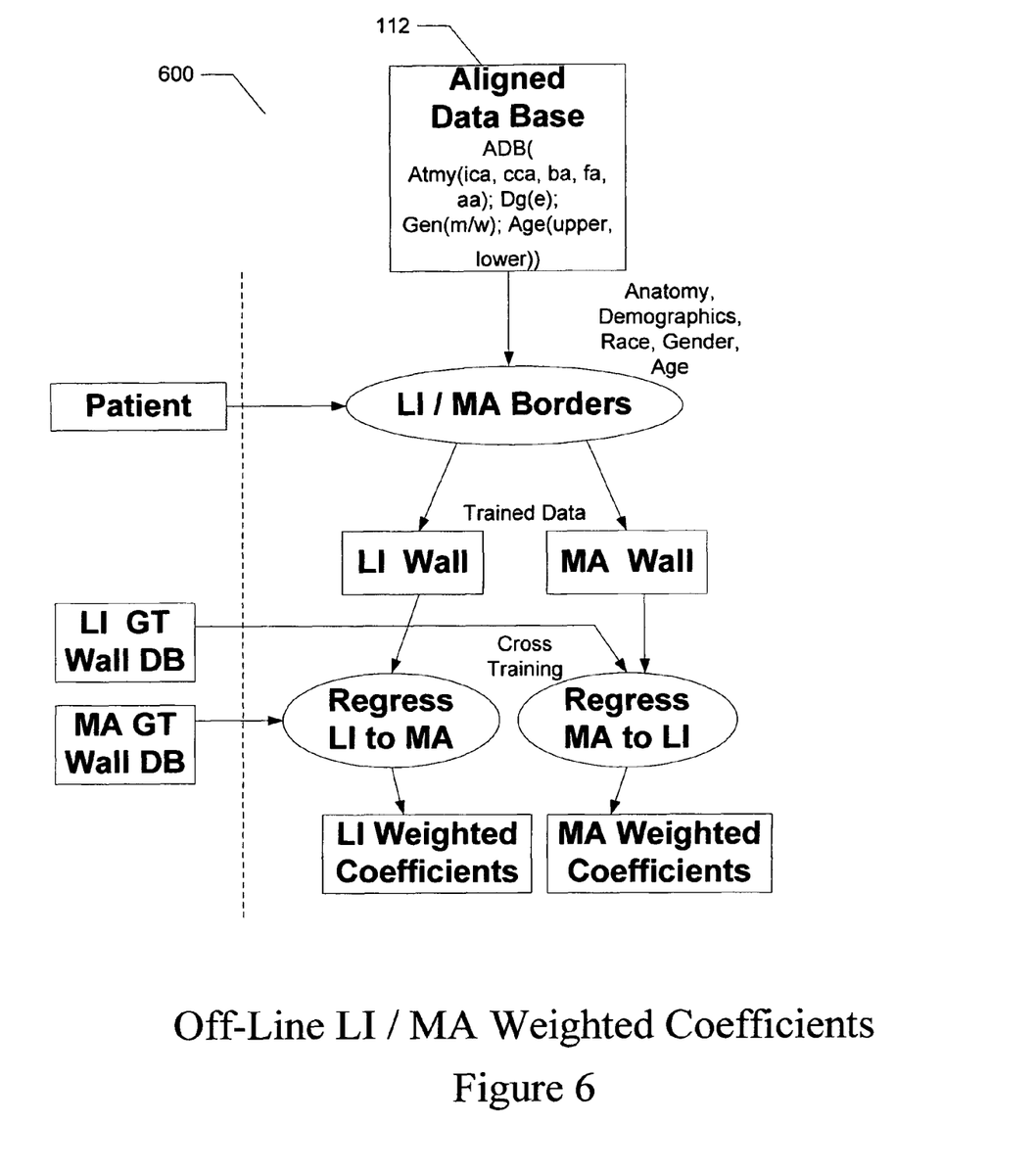
FIG. 6 illustrates an example embodiment of the LI/MA Weighted Offline Coefficient Estimation System.

Referring again to FIG. 2, the CAIMT 120 includes a dependency sub-system 240, where the intelligent coefficients of LI-to-MA (generated offline) are cross-multiplied with observed LI boundaries computed on-line for the incoming patient. This allows stretching the LI/MA boundary to MA/LI boundaries using the intelligence database. The intelligent coefficients of LI-to-MA are generated offline by an LI/MA weighted Offline Coefficient Estimation System 600 as shown in FIG. 6. This sub-system 600 allows computing the "LI-to-MA" weighted coefficients. This offline estimation is based on the concept of collecting the intelligence and generating the information which is needed by the CAIMT 120.

Figure 7:
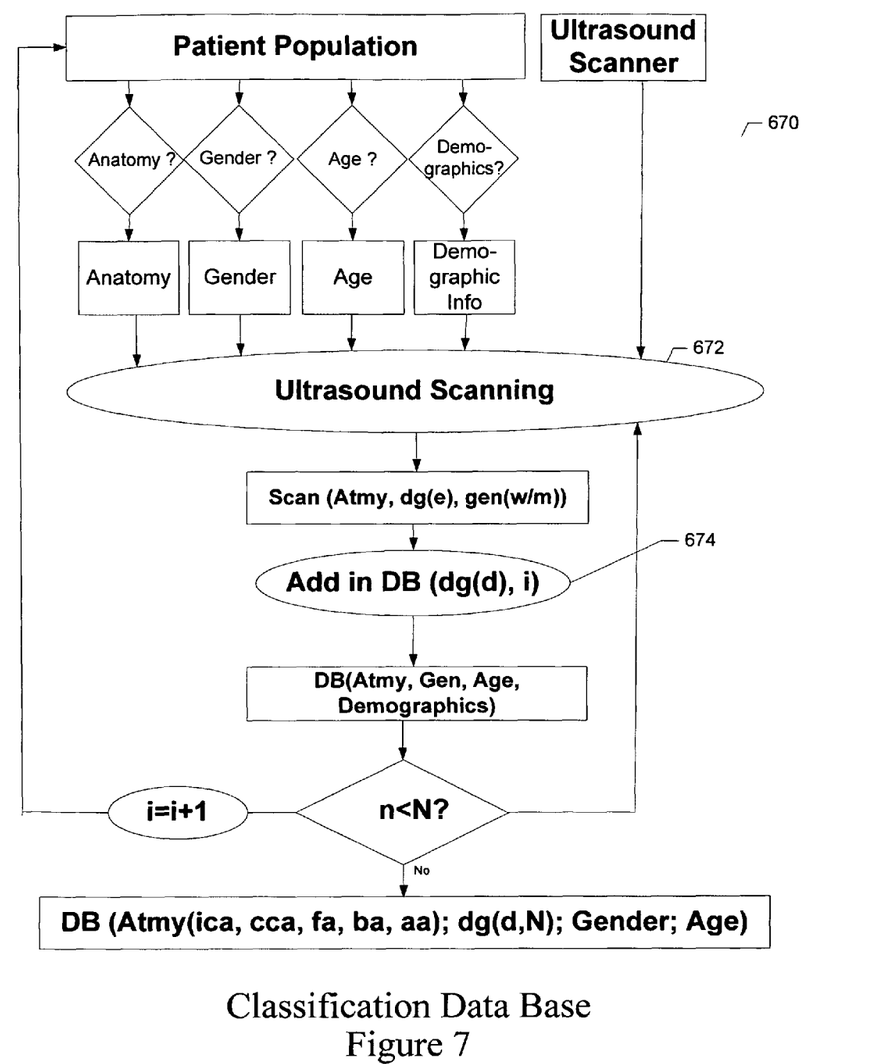
FIG. 7 illustrates an example embodiment of the Classification database system.
Figure 8:
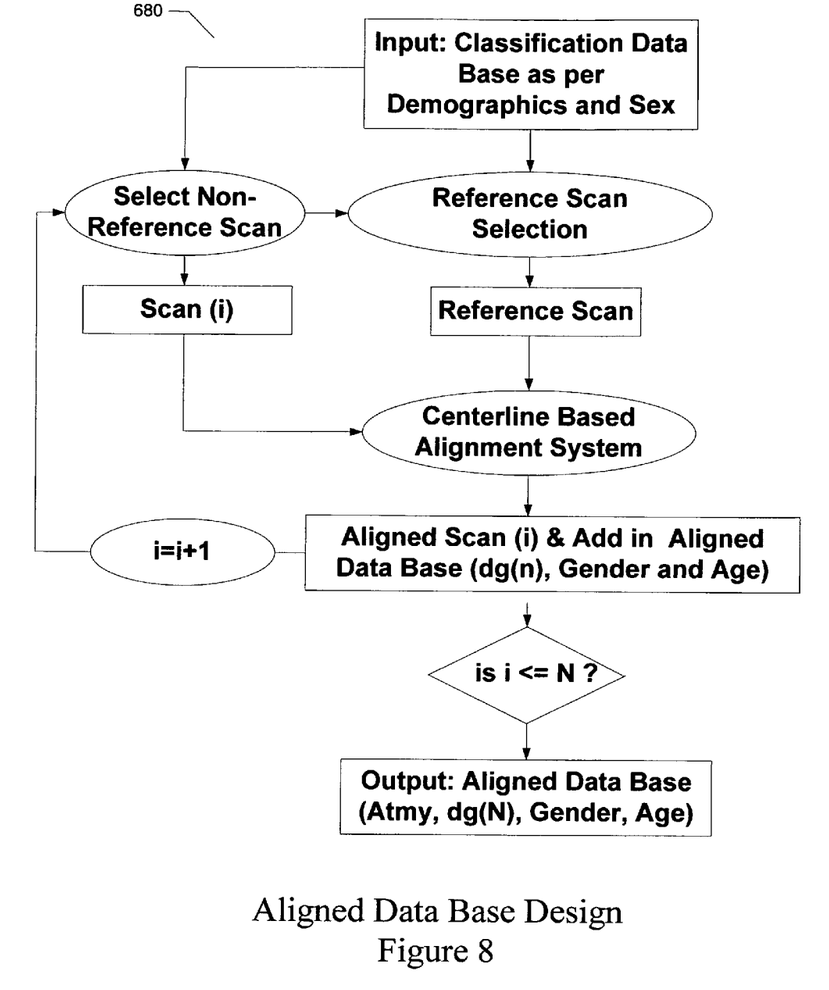
FIG. 8 illustrates an example embodiment of the Alignment database creation system.

Referring now to FIGS. 7 and 8, the structure and creation of the classification and alignment databases 112 in an example embodiment are shown. As illustrated in FIG. 7, a clinical site first builds the database. With a new incoming patient, the patient's anatomy, ethnicity, gender and age are recorded while pooling the scan images with a plurality of subjects in that database by using processes 672 and 674. Thus, for example, if there are 5 anatomies, 5 ethnic groups, 2 genders, and 5 age groups, then we will have 250 databases: 5×5×2×5=250 databases or 250 portions or dimensions of the same database. These different databases are represented as: DB(atmy (ica, cca, fa, ba, aa), dg(e), age(lower, upper), gender (m/w)), where "e" can take the value of: 1, . . . 5 or an ethnicity enumeration, gender takes the value of 1 or 2 or a gender enumeration, and age takes the value of 1, . . . 5 or an age enumeration. This data representation can be site dependent. If there are "s" clinical sites, one can obtain s times DB(atmy (ica, cca, fa, ba, aa), dg(e), age(lower, upper), gender (m/w)) different data representations for the various clinical sites, which in this example is s*250. This classification database representation 670 is illustrated in FIG. 7.

As illustrated in FIG. 8, an example process 680 in an embodiment allows for the creation of the alignment database system 112, where all the databases are aligned. Given the classification database representation 670 as described above, DB(atmy (ica, cca, fa, ba, aa), dg(e), age(lower, upper), gender (m/w)), one can use the alignment procedure 680 with respect to the centerline data as captured earlier and create a new alignment database 112 with reference to the centerline alignment. The alignment database 112 has a one-to-one correspondence with respect to the classification database. If there are N images in the classification database, the alignment database 112 will consist of N−1 images in the alignment database 112. The output of the alignment database 112 can be represented by: ADB(atmy (ica, cca, fa, ba, aa), dg(e), age(lower, upper), gender(m/w)). If there are "s" number of clinical sites, we will have s * alignment databases.

Therefore, various embodiments of a system and method for creating and using intelligent databases for assisting in intima-media thickness (IMT) measurements are disclosed. The various embodiments disclosed herein provide a number of advantages over conventional systems and methods. These advantages include:

(i) Integration of demographics for IMT measurement: IMT estimation integrates image and signal processing while taking the demographics, such as anatomy, ethnicity, race, age and gender into consideration. This patient demographic information makes the IMT measurement more robust and accurate.

(ii) Ethnicity and Race: Because the atherosclerosis build up has a demonstrated relationship with respect to ethnicity and race, this information helps in the classification of different databases.

(iii) Gender: Because the atherosclerosis build up in arteries of carotids, coronaries and aorta is linked with gender, this information further helps in the classification of different databases.

(iv) Age: Although the atherosclerosis build up does not bear a direct linear relationship with age, nevertheless, given a certain race, ethnic background, and gender, one can sub-classify and refine the databases with age as well. This leads to further scuttle refinement.

(v) Mimicking Protocol embedded into the form of training set: The mimicking concept of the sonographer or vascular surgeon or radiologist is incorporated in the IMT estimation process by so called training-data. This training data is actually classified as intelligent database design.

(vi) Transformation of the radiologist's training into computerized training method: If a vascular surgeon had to draw the IMT borders of LI and MA, the process would be to zoom the image to high enough resolution microscopically, use the expert's experience and judgment to trace the borders. This experience and judgment is captured by the training system and applied to new test patients who present for scanning and analysis of plaque burden for Atherosclerosis monitoring.

(vii) Need for a Reference Region during Training System Design: While preparing the intelligent knowledge base, the reference marker or guiding marker used is the region information which is well established. Thus, the choice of the region is a very important factor for building the intelligent database system.

(viii) Centerline as Reference Marker: For geometric shapes with varying topological changes or irregularity, one needs a symmetry concept. Symmetry or centerlines are ideal for irregular shapes. In one embodiment described herein, the centerline method is used as a reference marker.

(ix) Use of Distance Transform Method for Computation of Centerline: Calculus based methods are sensitive to end points which in turn are dependent upon image processing methods. In one embodiment described herein, we use distance transform, a geometric method which is very stable and accurate. This method is robust and is independent of the shape topology and changes like bifurcation.

(x) Speed of Centerline Computation: Distance transform methods are very fast and can take advantage of the digital nature of the data points in the image.

(xi) Alignment of images during the training data design: The alignment process uses centerline of the lumen region. Since the centerline captures the geometry's center of the blood vessel accurately, the alignment is robust.

(xii) Fixed Reference for Intelligence Database selection: The art of selection of the vessel which is straight in the image is an important criterion and offers the advantage of IMT challenges.

(xiii) Selection of the vessel which is straight: The concept of finding the vessel in the database which is straight or horizontal is new. It puts fewer burdens on the system and algorithm design.

(xiv) Art of computing the straight vessel: The concept of finding the straightness of the vessel.

(xv) Art of finding the Curvature of the vessel: The art of finding the radius of curvature of the centerline of the blood vessel.

(xvi) Art of Selection of best three vessels which are straight in the database: Based on the radius of curvature of the vessel, one can estimate the centerline, then the radius of curvature of all the blood vessels and then do a sorting which will then allows to select the best three vessels which have highest radius of curvature.

(xvii) Art of selection of the "reference vessel" in the database which has the highest signal-to-noise (SNR) and highest radius of curvature: Because we have few vessels in the database which are straight, we select the vessel which has least SNR value in the center of the image and thus the highest SNR for the reference vessel. The SNR evaluation of the image aids in selecting the reference image that gives us the advantage of a correct reference image.

(xviii) Lumen edge which aids in computation of Centerline: For centerline estimation (for reference mark generation, which is used for alignment of images for intelligent database creation), the lumen edges need to be determined. These edges are for the far and near end of the artery or tubular structure. These edges can be computed by convolving the High order derivatives of Gaussian Function with the down sampled image of the carotid scan.

(xix) Gaussian Function's Standard Deviation: Because the system uses the down sampling method, the blood vessel diameter can be captured using the higher order derivatives of the Gaussian kernel. Thus, the edges are very robust.

(xx) Automated Method of computation of Standard Deviation of Gaussian Kernel: The down sampling method allows an automated way to compute the standard deviation of the kernel, which as a result allows one to estimate the edge of the lumen.

Figure 9:
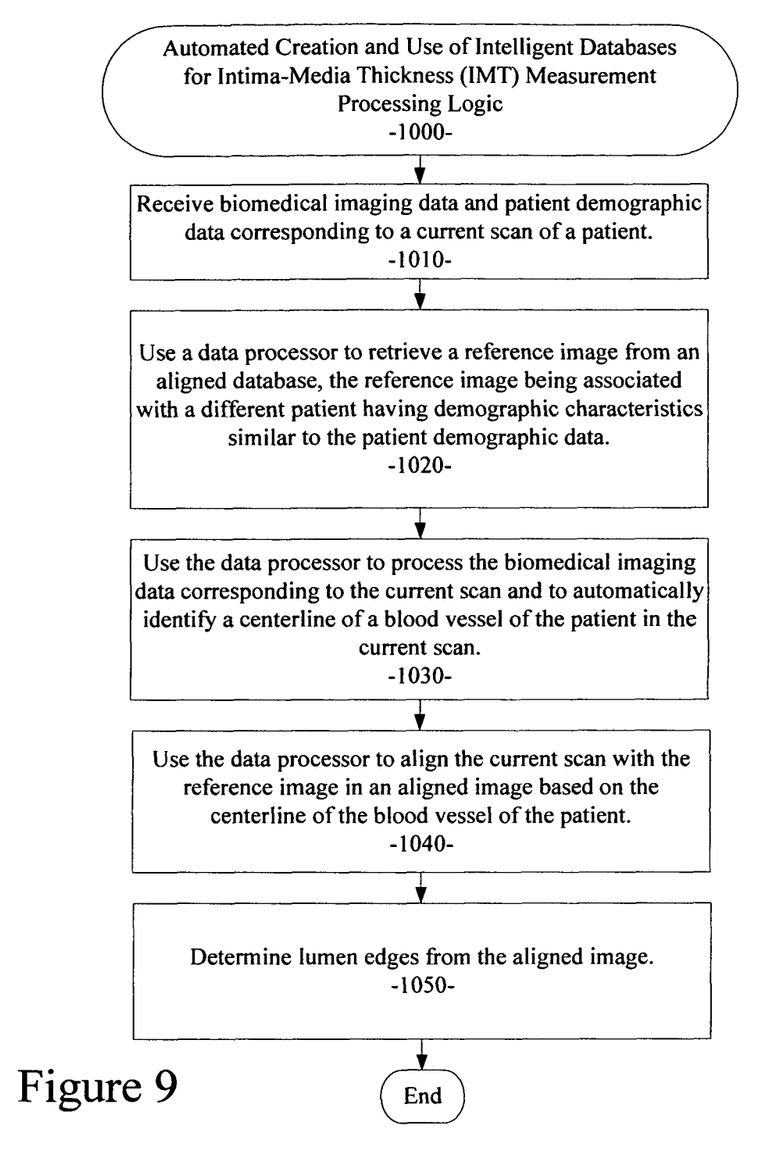
FIG. 9 is a processing flow chart illustrating an example embodiment of an automated system for creating and using intelligent databases for assisting in intima-media thickness (IMT) measurements as described herein.

FIG. 9 is a processing flow diagram illustrating an example embodiment of a system and method for creating and using intelligent databases for assisting in intima-media thickness (IMT) measurements as described herein. The method of an example embodiment includes: receiving biomedical imaging data and patient demographic data corresponding to a current scan of a patient (processing block 1010); using a data processor to retrieve a reference image from an aligned database, the reference image being associated with a different patient having demographic characteristics similar to the patient demographic data (processing block 1020); generating a first image using the Atherosclerosis burden data corresponding to the current scan, the first image providing a visualization of the Atherosclerosis burden corresponding to the current scan of the patient (processing block 1030); receiving Atherosclerosis burden data corresponding to a previous scan of the patient (processing block 1040); and generating a second image by fusing image data corresponding to the Atherosclerosis burden data of the previous scan with the first image, the second image providing a visualization of a change in the Atherosclerosis burden between the previous scan of the patient and the current scan of the patient (processing block 1050).

Figure 10:
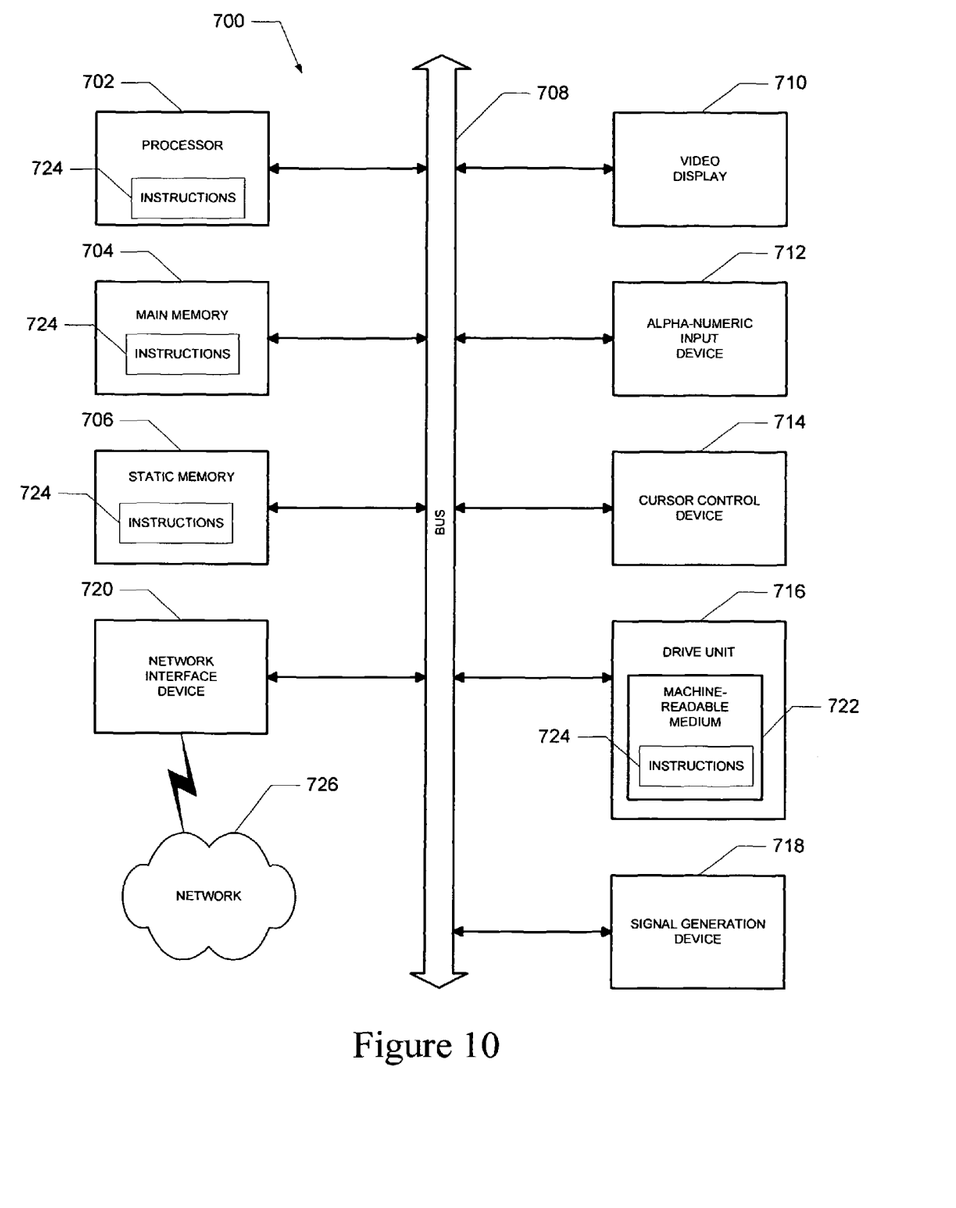
FIG. 10 shows a diagrammatic representation of machine in the example form of a computer system within which a set of instructions when executed may cause the machine to perform any one or more of the methodologies discussed herein.

FIG. 10 shows a diagrammatic representation of machine in the example form of a computer system 700 within which a set of instructions when executed may cause the machine to perform any one or more of the methodologies discussed herein. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated, the term "machine" can also be taken to include any collection of machines that individually or jointly execute a set (or multiple sets) of instructions to perform any one or more of the methodologies discussed herein.

The example computer system 700 includes a processor 702 (e.g., a central processing unit (CPU), a graphics processing unit (GPU), or both), a main memory 704 and a static memory 706, which communicate with each other via a bus 708. The computer system 700 may further include a video display unit 710 (e.g., a liquid crystal display (LCD) or a cathode ray tube (CRT)). The computer system 700 also includes an input device 712 (e.g., a keyboard), a cursor control device 714 (e.g., a mouse), a disk drive unit 716, a signal generation device 718 (e.g., a speaker) and a network interface device 720.

The disk drive unit 716 includes a machine-readable medium 722 on which is stored one or more sets of instructions (e.g., software 724) embodying any one or more of the methodologies or functions described herein. The instructions 724 may also reside, completely or at least partially, within the main memory 704, the static memory 706, and/or within the processor 702 during execution thereof by the computer system 700. The main memory 704 and the processor 702 also may constitute machine-readable media. The instructions 724 may further be transmitted or received over a network 726 via the network interface device 720. While the machine-readable medium 722 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" can also be taken to include any medium that is capable of storing, encoding or carrying a set of instructions for execution by the machine and that cause the machine to perform any one or more of the methodologies of the various embodiments, or that is capable of storing, encoding or carrying data structures utilized by or associated with such a set of instructions. The term "machine-readable medium" can accordingly be taken to include, but not be limited to, solid-state memories, optical media, and magnetic media.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

We claim:

1. A computer-implemented method comprising:
    receiving biomedical imaging data and patient demographic data corresponding to a current scan of a patient;
    using a data processor to create an off-line aligned database based on a common feature present in the biomedical imaging data;
    using the data processor to create off-line lumen-intima and media-adventitia coefficients for use as dependency linear or non-linear coefficients for on-line lumen-intima and media-adventitia borders;
    using the data processor to retrieve a reference image from the off-line aligned database, the reference image being associated with a different patient having demographic characteristics similar to the patient demographic data;
    using the data processor to process the biomedical imaging data corresponding to the current scan and to automatically identify a centerline of a blood vessel of the patient in the current scan;
    using the data processor to align the current scan with the reference image in an aligned image based on the centerline of the blood vessel of the patient;
    using the data processor to compute the initial lumen-intima and media-adventitia borders in the current scan using the multi-resolution approach; and
    using the data processor to regress the initial lumen-intima and media-adventitia borders of the current scan using the off-line linear and non-linear coefficients.

2. The method as claimed in claim 1 wherein the biomedical imaging data comprises two-dimensional (2D) longitudinal B-mode ultrasound images.

3. The method as claimed in claim 1 wherein the demographic data includes data related to the patient and selected from the group: ethnicity, gender, and age.

4. The method as claimed in claim 1 including using the aligned image to generate intima-media thickness (IMT) data.

5. The method as claimed in claim 1 including using data from the aligned database to generate intima-media thickness (IMT) data.

6. The method as claimed in claim 1 including using the aligned image to determine a level cardiovascular disease in the patient.

7. The method as claimed in claim 1 including using data from the aligned database to determine a level cardiovascular disease in the patient.

8. The method as claimed in claim 1 including using dependency coefficients created from data in the aligned database for determining lumen or MA edges.

9. The method as claimed in claim 1 wherein the lumen edges are determined using a multi-resolution scale-space methodology.

10. The method as claimed in claim 1 wherein the aligned database includes a classification database that includes data representing demographic characteristics of a plurality of groups of subjects.

11. A computer-implemented method comprising:
    receiving biomedical imaging data and patient demographic data corresponding to a plurality of subjects;
    using a data processor to process the biomedical imaging data and patient demographic data and to automatically organize the biomedical imaging data and patient demographic data into groups based on a plurality of demographic characteristics;
    using the data processor to create biomedical imaging data into groups of age, gender, vascular anatomy and demographics;
    using the data processor to select the off-line reference image from a database;
    using the data processor to align the off-line biomedical imaging data with respect to an off-line reference image to create an aligned database based on a common feature present in the biomedical imaging data; and
    using the data processor to create an aligned database for each of the demographics groups.

12. The method as claimed in claim 11 wherein the biomedical imaging data comprises two-dimensional (2D) longitudinal B-mode or RF ultrasound images,.

13. The method as claimed in claim 11 wherein the demographic data includes data selected from the group: ethnicity, gender, and age.

14. The method as claimed in claim 11 including using, data from the aligned database to generate intima-media thickness (IMT) data.

15. The method as claimed in claim 11 including using data from the aligned database to determine a level cardiovascular disease in a patient.

16. The method as claimed in claim 11 including creating dependency coefficients from data in the aligned database for determining lumen or MA edges.

17. The method as claimed in claim 11 wherein the aligned database includes a classification database that includes data representing demographic characteristics of a plurality of groups of subjects.

18. A system, comprising:
    a data processor;
    a database, in data communication with the data processor, for storage of imaging information; and an automated intima-media thickness (IMT) measurement module, executable by the data processor, to:
receive biomedical imaging data and patient demographic data corresponding to as current scan of a patient;
use the data processor to retrieve a reference image from an aligned database, the reference image being associated with a different patient having demographic characteristics similar to the patient demographic data;
use the data processor to process the biomedical imaging data corresponding to the current scan and to automatically identify a centerline of a blood vessel of the patient in the current scan;
use the data processor to align the current can with the reference image in an aligned image based on the centerline of the blood vessel of the patient;
use the data processor to regress linearly or nonlinearly the online lumen-intima and media-adventitia interfaces using the off line lumen-intima and media-adventitia interfaces; and
determine IMT values in the current scan.

19. The system as claimed in claim 18 wherein the biomedical imaging data comprises two-dimensional (2D) longitudinal B-mode or RF ultrasound images.

20. A machine-useable storage media/embodying instructions which, when executed by a machine, cause the machine to:
receive biomedical imaging data and patient demographic data corresponding to a current scan of a patient;
use the data processor to retrieve a reference image from an aligned database, the reference image being associated with a different patient having demographic characteristics similar to the patient demographic data;
use the data processor to process the biomedical imaging data corresponding to the current scan and to automatically identify a centerline of a blood vessel of the patient in the current scan;
use the data processor to align the current scan with the reference image in an aligned image based on the centerline of the blood vessel of the patient;
use the data processor to regress linearly or nonlinearly the online lumen-intima and media-adventitia interfaces using the off-line lumen-intima and media-adventitia interfaces; and
determine IMT values in the current scan.

21. The machine-useable storage medium as claimed in claim 20 wherein the biomedical imaging data comprises two-dimensional (2D) longitudinal B-mode or RF ultrasound images.

* * * * *